(12) United States Patent
Matzan

(10) Patent No.: US 6,934,029 B1
(45) Date of Patent: Aug. 23, 2005

(54) DUAL LASER WEB DEFECT SCANNER

(76) Inventor: Eugene Matzan, 2187 N. Washington St., Rochester, NY (US) 14625

(*) Notice: Subject to any disclaimer, the term of this patent is extended or adjusted under 35 U.S.C. 154(b) by 315 days.

(21) Appl. No.: 10/356,940

(22) Filed: Feb. 3, 2003

Related U.S. Application Data

(60) Provisional application No. 60/374,275, filed on Apr. 22, 2002.

(51) Int. Cl.[7] .................................. G01N 21/84
(52) U.S. Cl. ........................................ 356/430
(58) Field of Search ........................... 356/429–431, 356/237.1–237.5; 250/571, 572

(56) References Cited

U.S. PATENT DOCUMENTS

| | | | | |
|---|---|---|---|---|
| 4,265,545 A | * | 5/1981 | Slaker | 356/431 |
| 4,302,108 A | * | 11/1981 | Timson | 356/450 |
| 4,570,074 A | * | 2/1986 | Jette | 250/559.49 |
| 4,775,238 A | * | 10/1988 | Weber | 356/431 |
| 6,097,482 A | * | 8/2000 | Smith et al. | 356/237.1 |
| 6,166,393 A | * | 12/2000 | Paul et al. | 250/559.08 |
| 6,630,995 B1 | * | 10/2003 | Hunter | 356/237.5 |

* cited by examiner

Primary Examiner—Michael P. Stafira

(57) ABSTRACT

A dual laser web scanner is disclosed designed to detect defects in all types of webs and flat sheet materials, e.g., metal, plastic, textiles, paper, film, and others. The scanner can be used on opaque and transparent materials. Compared to the existing web scanners, the subject scanner offers a simplified detection system, as well as, greater resolution, accuracy and repeatability. A focusing lens images the two beams onto an optical scanner. The two beams are therefore periodically deflected and imaged through an F-theta lens onto to surface of the web being scanned. The scanning occurs transversely to the direction of the web movement. The flying spots generated by the laser beams are situated one above the other in the direction parallel to the direction of the web movement. As the two beams scan the web and encounter a defect such as an inclusion, surface dirt, a hole, or a wrinkle, the intensity of light reflected (or transmitted if the material is transparent or translucent) from the leading spot if the web will be different than the intensity of the trailing spot. Two separate photo detectors detect the return light. When the flying spots are instantaneously located in any area of the web where there is no defect, the intensities of the detected light are substantially identical. The magnitude of the detected light intensity from both flying spots is electronically compared and, when a difference is detected, a signal is generated indicting the occurrence of a defect.

20 Claims, 4 Drawing Sheets

DUAL LASER WEB DEFECT SCANNER

This application claims priority to my provisional application 60/374,275 filed Apr. 22, 2002.

FIELD OF THE INVENTION

The instant invention relates generally to systems for scanning of webs and flat sheet materials (all called "webs") intended to locate any flaws, defects, non-uniformities, or deviations from the desired physical properties.

BACKGROUND OF THE INVENTION

Numerous manufacturing processes involve different type of webs, i.e., generally thin, flat, flexible materials intended for transfer from one roll or a spool to another roll or a spool. Such materials may be sheet metals, paper, plastic, film, and textiles. Prior to processing materials in web form are inspected. Optical inspection is intended to detect surface defects, imperfections and flaws. The surface of the web is scanned using lasers or video cameras and any defects are detected and their location on the surface of the material is noted. The defective areas can them be repaired, excised, or avoided in subsequent processing.

In many applications use of lasers for scanning the web surface has advantages in terms of speed; resolution and accuracy vs. video cameras, and many systems have been patented involving laser scanning. For example, U.S. Pat. No. 3,900,265 describes a "Laser Scanner Flaw Detection System". This system uses a single laser and rather complex electronics to detect the presence of defects and determine their location. Other inventions claim similar systems also using single lasers.

SUMMARY OF THE INVENTION

The invention being described here for automated inspection of flat materials such as webs and sheets, has several important advantages over the prior art in that it permits the use of a significantly simplified and lower cost electronics system, provides for unambiguous detection of defects and faults, determination of the size, shape and location of such defects, and, compared to single laser systems, a greater resolution. The use of semiconductor diode lasers, instead of gas lasers, as in the older systems, makes the system more compact and more rugged, important considerations for use on manufacturing floors.

DESCRIPTION OF THE PREFERRED EMBODIMENT

Figure 1:
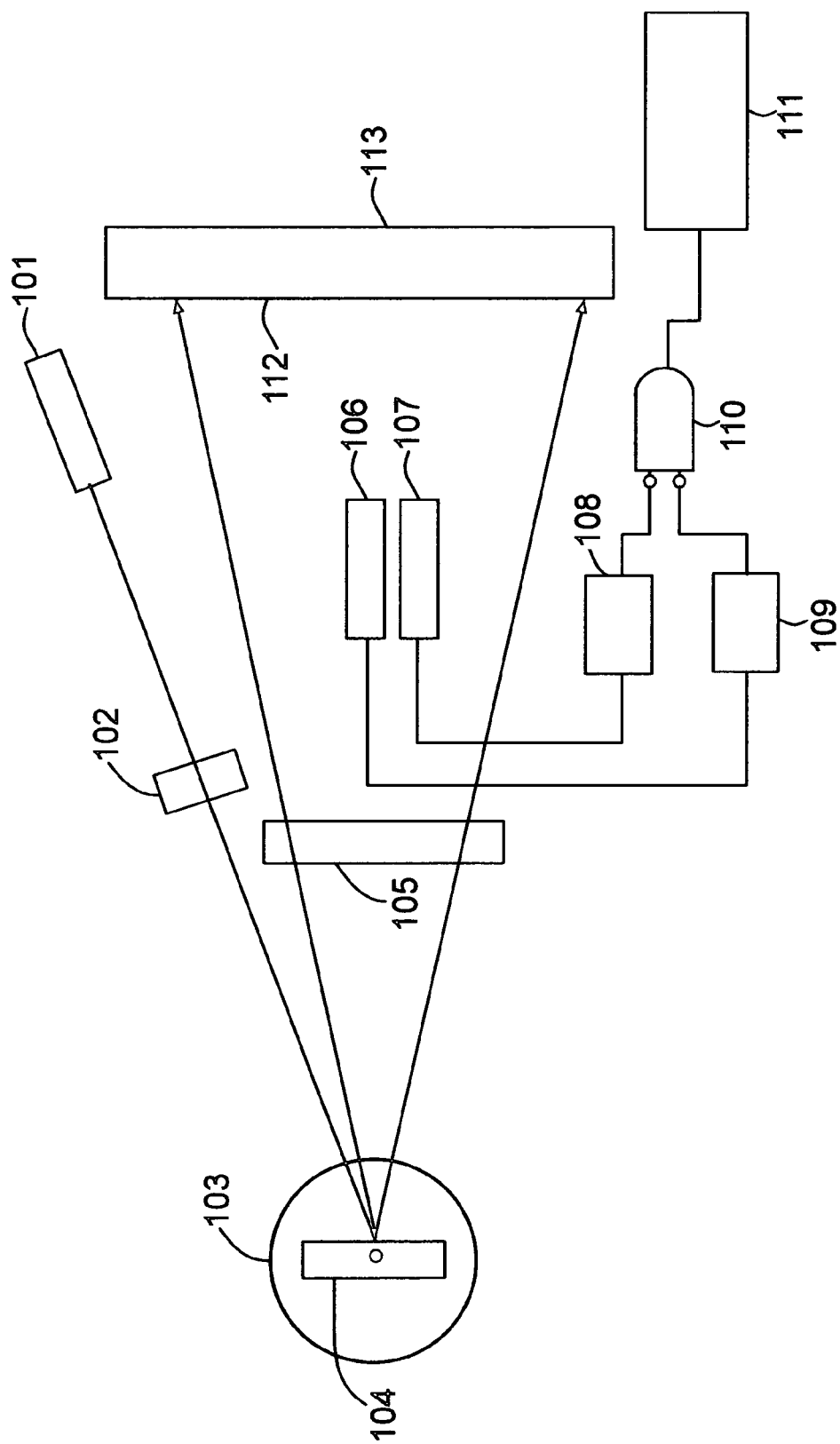
FIG. 1 is a schematic diagram of the system as viewed from the top.

Referring now to FIG. 1, which is a simplified schematic diagram of the dual laser web scanner for opaque materials, in which the optical system is depicted as being viewed from the top. 112 is the web being moved from the roll 113 to another roll (not visible in this drawing). Laser 101 (the second laser is not depicted in this drawing) emits a beam of light that is focused by the lens 102 onto the mirror 104 of scanning means 103. Those skilled in the art will understand that said scanning means could be a galvanometer, a rotating segmented mirror or a hologon used to achieve the same effect. The scanning means 103 periodically deflects the incoming beam of light through an F-theta lens 105 onto the surface 112 of the web. The purpose of the F-theta lens is to maintain the resulting flying spot of light on said surface of the web in focus for all angles of deflection. Depending on the type of the web material, laser light is reflected or scattered from the web surface.

Figure 2:
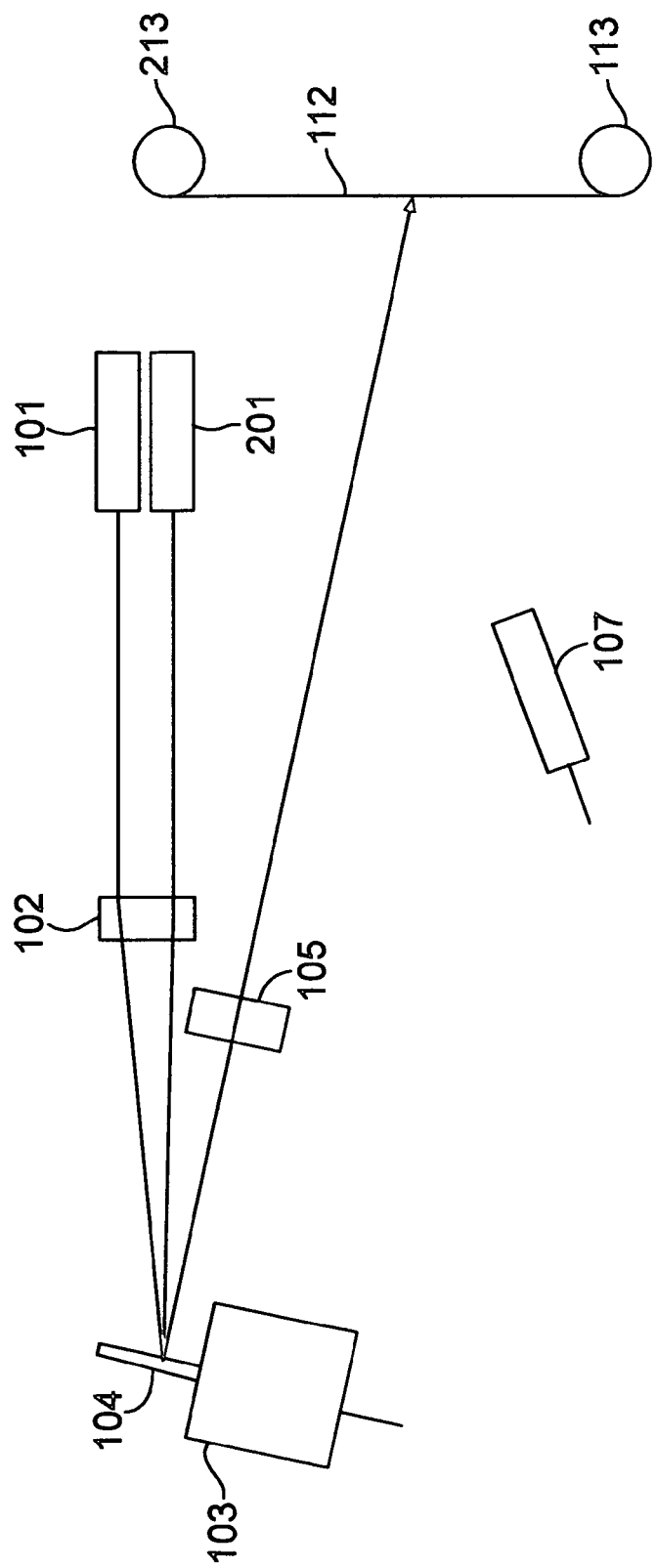
FIG. 2 is a schematic diagram of the system as viewed from the side.

With reference to FIG. 2, which is a simplified schematic diagram of said dual laser web scanner, in which the optical system is depicted as being viewed from the side, both lasers 101 and 201 are now visible. Both said lasers are solid state diode lasers, each emitting light of different color (wavelength), for example, the laser 101 emitting a beam of red light and the laser 201 emitting a beam of green light, though it is understood that other colors could be used. The reason for using two different colors is to provide a means for discrimination between the two resulting flying spots generated on the web surface. In addition, the laser light could be amplitude modulated or pulse modulated to provide other means for discrimination. Both said beams pass through said F-theta lens 105 as explained above. The lens is designed such that it focuses well the laser light of both colors. Alternately, a lens assembly comprising two separate F-theta segments could be used.

Figure 4:
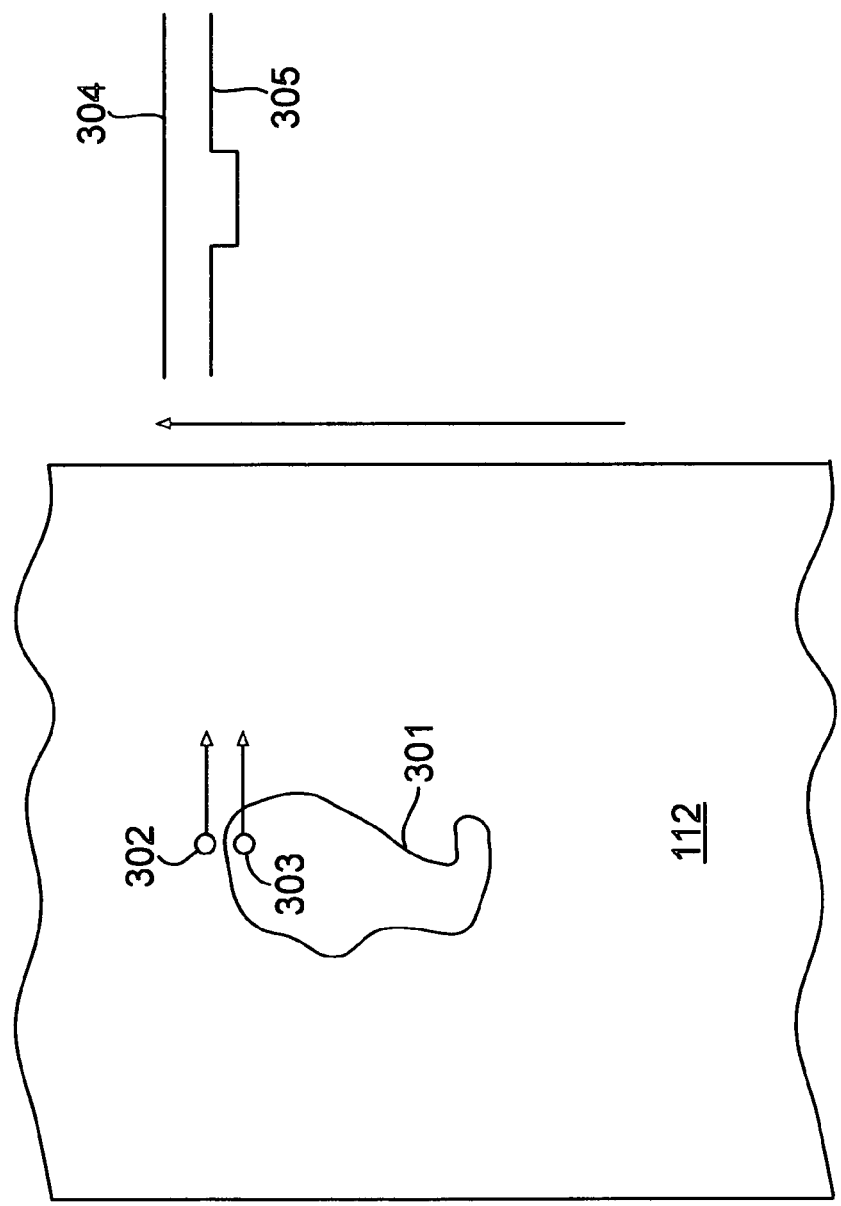
FIG. 4 is an example of detection of a defect in a web and the resulting waveforms.

As shown in FIG. 4, the flying spots 302 and 303 appear one above the other aligned to coincide with the indicated direction of the web travel. Thus, as shown in this drawing, flying spot 303 is leading and intercepts the blemish 301 first. Flying spot 302 intercepts said blemish second.

FIG. 1 shows two photo-detectors means 106 and 107. Each said photo-detector means comprises optics that image a section said web surface onto the photo-sensitive surface of a photo-detector and a color filter that passes light from only one of said flying spots. Said photo-detectors can be photo-multipliers, photo tubes, avalanche diodes, or photo-diodes. The photo-detectors generate electrical signals in response to the light received from said flying spots. Such are shown as an example in FIG. 4. The signals are amplified by amplifiers and amplitude discriminators 108 and 109 and are then fed into an anticoincidence circuit 110 depicted by a NAND gate. The gate generates an output signal if, and only if, the intensity of the light reflected or scattered from one flying spot differs sufficiently to pass one of the amplifiers and amplitude discriminators 108 and 109. The purpose of the amplitude discriminators, which, for example, could be Schmitt triggers, is to prevent any noise or negligible defects on the web surface from triggering fault detection. The output signal from the NAND gate 110 signifies that an intercept of a blemish, defect, imperfection or a fault on the web surface has occurred. This signal is passed into a computing means 111, which also receives data representing the instantaneous position of the flying spots from the scanning means 103. The computing means, which can be a microprocessor or a computer, processes said signals and generates information on the size and shape of the blemish and its location. Using an alternate circuit, if the amplitude of the intercept signals is preserved, rather than generating intercept signals of uniform amplitude, said computing means could also infer the nature of the defect from the amplitude and polarity of the intercept signals.

The results generated by the computing means 111 can be displayed, recorded or otherwise used to appropriately deal with the fault, defect or blemish.

Should amplitude or pulse modulation of said lasers 101 and 201 be used as the means for discrimination instead of or in addition to color, blocks 108 and 109 could incorporate appropriate frequency filters or synchronous phase detectors to separate the light reflected from the flying spots coming from the photo-detector means 106 and 107.

Again referring to FIG. 4, the detection of defects that appear on the surface of the web material occurs as follows:

The flying spots 302 and 303 scan the surface of the web transverse to the direction of the web movement. The leading flying spot 303 first encounters and intercepts the defect 301. The photo-detector means 107 of FIG. 1 detects the change in light intensity reflected from the flying spot 303 and, in response, generates an electronic signal 305, while the flying spot 302 still illuminates the defect-free surface of the web, and hence the corresponding photo-detector means 106 does not generate a signal as depicted in the trace 304. If the amplitude of the signal 305 exceeds a certain minimum level as determined by the amplitude discriminator 108, the signal passes to the NAND gate 110, which, in turn, generates an output signal indicating the initial intercept. The coordinates of this initial intercept are generated by said scanning means and the entire initial intercept is stored in the memory of said computing means 111 (FIG. 1) as a sequence of timing pulses. When the trailing flying spot 302 intercepts the defect, it also generates an intercept. The spacing of the flying spots is so arranged that this new intercept scans the surface at a location not previously scanned by the flying spot 303; thus the resolution is doubled. The scan continues and the intercepts are stored in the memory as they are acquired until the flying spot 303 enters a defect-free region of the web. At this point its corresponding trace will be as shown by 304, while the output corresponding to the flying spot 302 will still appear as the trace 305. As a result, the NAND gate 110 generates an output into the computing means 111, signifying the end of the defect scan. The accumulated intercepts are processed using algorithms of image analysis well known to those skilled in the art, to produce information on the size and shape of the defect, as well as it precise location.

Figure 3:
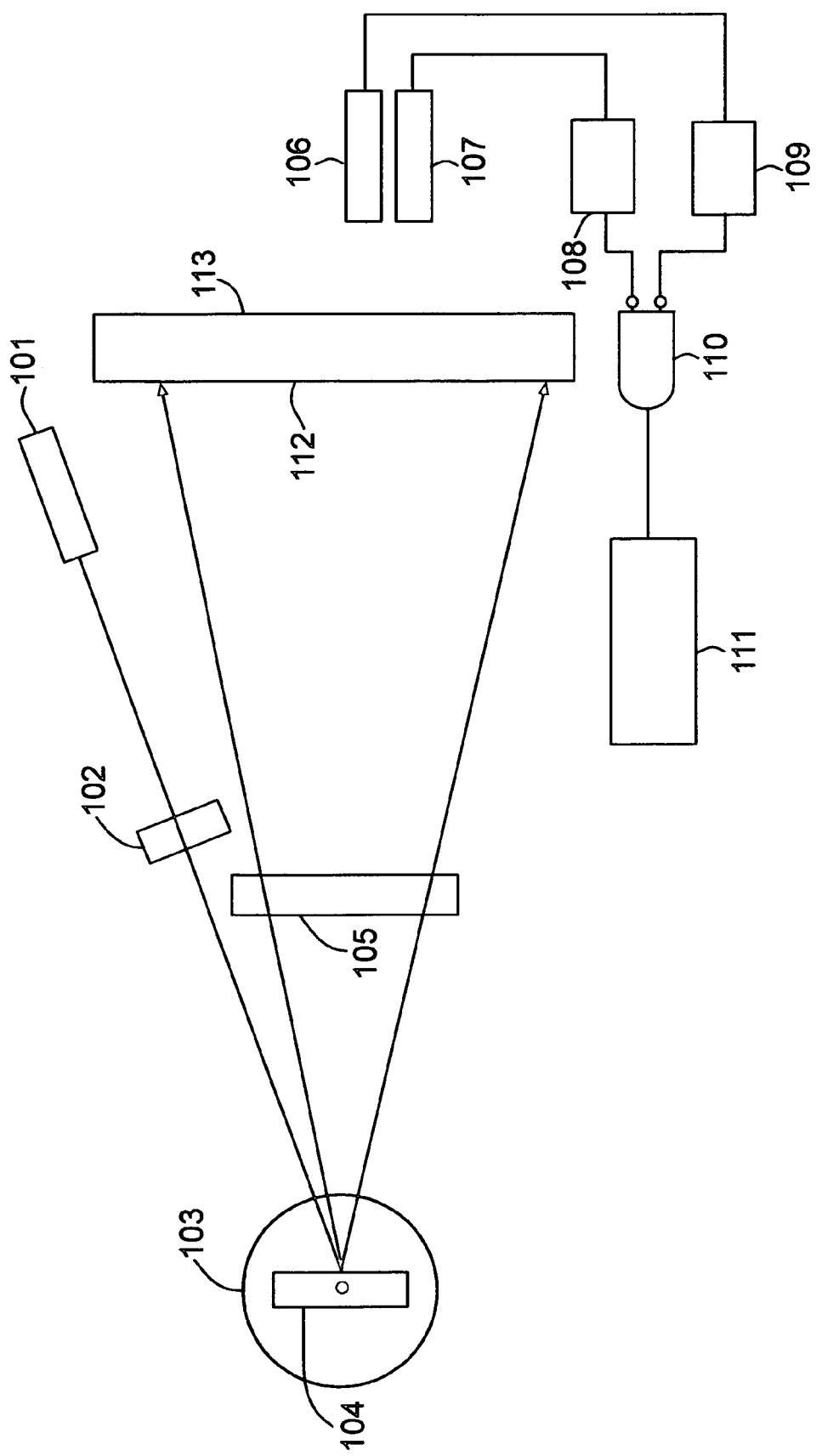
FIG. 3 is a schematic diagram of the system for use with transparent or translucent materials.

FIG. 3 schematically depicts an alternate optical configuration of the subject dual laser web scanner for use with transparent or translucent web materials. The difference between this configuration and the one shown in FIG. 1 is in that the photo-detector means in the former are located behind, rather than in the front of the web and thus detects transmitted, rather than reflected or scattered light.

The invention has been described herein in considerable detail in order to provide those skilled in the art with the information needed to apply to construct the apparatus subject of this invention. However, it is to be understood that the invention can be implemented using components and equipment different from those described herein and any number of alternatives and modifications can be introduced without departing from the scope and concept of the invention itself.

I claim:

1. A dual laser web defect scanner comprising
   at least two lasers,
   an optical scanning means for scanning a web having a reflective or scattering surface or a combination of such surface properties,
   optical means for focusing light beams generated by said lasers onto said surface of said web so as to enable said scanning means to scan said light beams across said web,
   at least two photoreceptive means separately responsive to light corresponding to different ones of said beams reflected or scattered from said flat material,
   at least two electronic signal processing means separately responsive to different ones of said photoreceptive means,
   means operated by said processing means, including signal comparative means,
   for providing outputs representing defects in said web.

2. The dual laser web defect scanner per claim 1 in which each said laser emits light of wavelength different of that of all other lasers in said web defect scanner.

3. The dual laser web defect scanner per claim 1 in which the light output of each of said lasers is amplitude-modulated by a periodically repetitive signal, each laser modulated by a signal of different frequency.

4. The dual laser web defect scanner per claim 1 in which the light output of each of said lasers is pulse-modulated by a periodically repetitive signal, each laser modulated by a signal of different repetition rate.

5. The dual laser web defect scanner per claim 1 in which said optical scanning means is a mirror galvanometer.

6. The dual laser web defect scanner per claim 1 in which said optical scanning means is a rotating segmented mirror.

7. The dual laser web defect scanner per claim 1 in which said optical scanning means is a hologon.

8. The dual laser web defect scanner per claim 1 in which said optical focusing means is an F-theta lens.

9. The dual laser web defect scanner per claim 1 in which the beams of said lasers reflected from said optical scanning means are parallel and closely spaced to each other.

10. The dual laser web defect scanner per claim 1 in which said photoreceptive means are photomultipliers.

11. The dual laser web defect scanner per claim 1 in which said photoreceptive means are phototubes.

12. The dual laser web defect scanner per claim 1 in which said photoreceptive means are photodiodes.

13. The dual laser web defect scanner per claim 1 in which said photoreceptive means are avalanche diodes.

14. The dual laser web defect scanner per claim 1 in which the photoreceptive means are situated to receive light reflected or scattered from the surface of said web or flat material.

15. The dual laser web defect scanner per claim 1 in which the photoreceptive means are situated to receive light transmitted though said web.

16. The dual laser web defect scanner per claim 1 in which the flying spots resulting from said laser beams illuminating the surface of said web are positioned to appear one above the other along the movement direction of said web.

17. The dual laser web defect scanner per claim 1 in which the output signals from said photoreceptive means are input into signal processing and amplifying means.

18. The dual laser web defect scanner per claim 1 in which said signal processing and amplifying means only pass signals the amplitude of which exceeds a minimum predetermined level.

19. The dual laser web defect scanner per claim 1 in which said defect output providing means includes logic means which compare the outputs of said signal processing means and generate an output when said outputs are different.

20. The dual laser web defect scanner per claim 1 in which said defect output providing means including computing means is programmed to determine from the signals acquired from said logic means the size and shape of said defects.

* * * * *